(12) United States Patent
Dreyfuss et al.

(10) Patent No.: US 8,764,797 B2
(45) Date of Patent: Jul. 1, 2014

(54) SUTURE ANCHOR WITH INSERT-MOLDED SUTURE EYELET

(75) Inventors: Peter J. Dreyfuss, Naples, FL (US);
William C. Benavitz, Naples, FL (US);
Reinhold Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1807 days.

(21) Appl. No.: 11/636,972

(22) Filed: Dec. 12, 2006

(65) Prior Publication Data

US 2007/0150003 A1 Jun. 28, 2007

Related U.S. Application Data

(63) and a continuation-in-part of application No. 10/083,568, filed on Feb. 27, 2002, now Pat. No. 7,226,469, which is a continuation-in-part of application No. 09/495,816, filed on Feb. 2, 2000, now Pat. No. 6,517,564.

(60) Provisional application No. 60/750,061, filed on Dec. 14, 2005.

(51) Int. Cl.
*A61B 17/04* (2006.01)

(52) U.S. Cl.
USPC .......................................... 606/232; 606/300

(58) Field of Classification Search
USPC ................................................ 606/232, 300
See application file for complete search history.

(56) References Cited

U.S. PATENT DOCUMENTS

| | | | |
|---|---|---|---|
| 4,632,100 A | 12/1986 | Somers et al. | |
| 5,370,662 A | 12/1994 | Stone et al. | |
| 5,569,306 A * | 10/1996 | Thal | 606/232 |
| 5,571,139 A * | 11/1996 | Jenkins, Jr. | 606/232 |
| 5,964,783 A | 10/1999 | Grafton et al. | |
| 6,517,564 B1 | 2/2003 | Grafton et al. | |
| 6,666,877 B2 * | 12/2003 | Morgan et al. | 606/232 |
| 2002/0087190 A1 | 7/2002 | Benavitz et al. | |
| 2003/0004545 A1 | 1/2003 | Burkhart et al. | |
| 2004/0106950 A1 | 6/2004 | Grafton et al. | |

FOREIGN PATENT DOCUMENTS

EP 1 300 115 4/2003

* cited by examiner

*Primary Examiner* — Corrine M McDermott
*Assistant Examiner* — Alexander Orkin
(74) *Attorney, Agent, or Firm* — Dickstein Shapiro LLP

(57) ABSTRACT

An insert-molded suture anchor with a biodegradable polymer body in which a loop of suture is totally contained within the polymer. The suture anchor body features a drive end that is shaped to be received into a recess in the end of a hand driver. Anchoring ribs are formed along the remaining length of the anchor. The loop of suture which includes and eyelet for attaching a suture strand is totally embedded within the anchor body during the insert-molding fabrication process. The anchor is produced by placing the suture in an injection mold, and injecting biodegradable polymer into the mold.

10 Claims, 7 Drawing Sheets

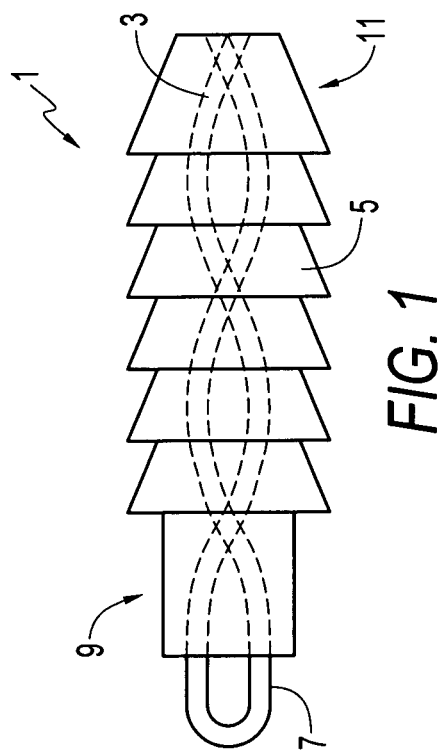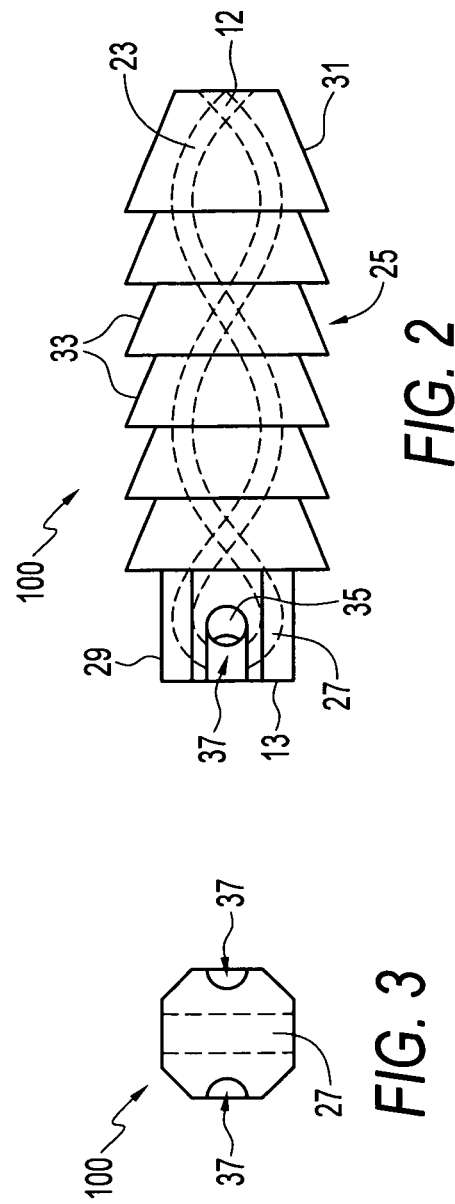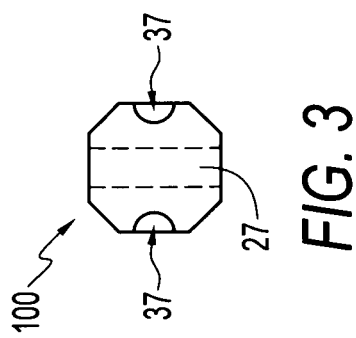

US 8,764,797 B2

SUTURE ANCHOR WITH INSERT-MOLDED SUTURE EYELET

CROSS-REFERENCE TO RELATED APPLICATIONS

This application claims the benefit of U.S. Provisional Application Ser. No. 60/750,061, filed Dec. 14, 2005, the disclosure of which is incorporated by reference herein in its entirety. This application is also a continuation-in-part of U.S. application Ser. No. 10/083,568, filed Feb. 27, 2002, now U.S. Pat. No. 7,226,469 which is a continuation-in-part of U.S. application Ser. No. 09/495,816, filed Feb. 2, 2000, now U.S. Pat. No. 6,517,564, the disclosures of which are also incorporated by reference herein in their entirety.

FIELD OF THE INVENTION

The present invention relates to apparatus and methods for surgically anchoring suture. More specifically, the present invention relates to surgically anchoring suture to bone using a suture anchor with a suture eyelet insert-molded directly within the suture anchor body.

DESCRIPTION OF THE RELATED ART

Surgical reattachment of soft tissue to bone is a common feature of orthopedic joint repair. Surgical reattachment is indicated when soft tissue tears partially or completely away from bone, for example. Various fixation devices, including suture, screws, staples, wedges, and plugs have been used in the past to secure soft tissue to bone. More recently, threaded and ribbed suture anchors also have been developed.

Suture fixation devices, such as anchors and other implants, generally include structure to which suture is attached or secured. U.S. Pat. No. 4,632,100, for example, discloses and claims a threaded suture anchor with a complex press-fitted disc and knot structure which secures the suture to the anchor. In other suture anchors, such as those disclosed in U.S. Pat. No. 5,370,662, the suture is attached to the anchor by passing the suture through an eyelet at the end of the anchor. Problems arise if the structure for attaching the suture fails postoperatively and the suture detaches from the anchor prematurely. In some of the known devices, the suture is also exposed to abrasion or cutting by sharp or rough areas along the walls of the bone canal into which the anchor is inserted.

In addition, the eyelet or, in the case of U.S. Pat. No. 4,632,100, the axial opening for receiving the disc to which the suture is knotted, is formed as part of the drive head of the known suture anchors. Forming openings through the drive head of the anchor mechanically weakens the drive head.

Various enhancements to the drive head can improve aspects of anchor performance. For example, recessed grooves may be formed on opposite sides of the drive head to receive and protect the suture from the abrasive areas of the suture anchor tunnel. These features, however, also tend to reduce integrity and weaken the drive head. The drive head can be made larger to recover lost mechanical strength lost. In general, however, small anchoring devices are preferred because they are less invasive and cause less trauma.

Insert-molding suture into an anchor such that a loop of suture extends from the head of the anchor is described in U.S. patent application Ser. No. 10/083,568. An example of the prior art suture anchor 1 is illustrated in FIG. 1. The suture anchor 1 includes a flexible strand 3 inside an anchor body 5. The flexible strand 3 preferably is formed into a loop and twisted. An exposed portion 7 of the loop extends outside the anchor body 5 at a drive end 9, opposite a tapered insertion end 11. The exposed portion 7 of the flexible strand 3 is shown formed into an eyelet to provide an attachment point used for tissue proximation and reattachment. Surgical situations require, however, smaller anchors that need a shallower pilot hole to provide increased protection of the suture loop.

Accordingly, a need exists for a suture anchor or implant to which suture is secured against detachment from the anchor and which protects a suture-attachment structure from abrasion and other damage. The protected suture-attachment structure would serve to extend anchor viability during surgical rehabilitation. A soft tissue fixation device configured with a low profile would be particularly useful for reattachment to the glenoid rim, for example.

SUMMARY OF THE INVENTION

The suture anchor of the present invention overcomes disadvantages of the prior art, such as those noted above, by providing a loop of suture entirely insert-molded within the suture anchor. The suture loop passes around an eyelet opening developed in the drive head. The suture anchor increases suture eyelet viability during rehabilitation. The suture anchor also requires less pilot hole depth than prior devices.

Other features and advantages of the present invention will become apparent from the following description of the invention, which refers to the accompanying drawings.

BRIEF DESCRIPTION OF THE DRAWINGS

FIG. 1 is a plan view of an insert-molded suture anchor as disclosed in a parent patent application;

FIG. 2 is plan view of a suture anchor according to the present invention;

FIG. 3 is a proximal end view of the suture anchor of FIG. 2;

DETAILED DESCRIPTION OF THE PREFERRED EMBODIMENTS

Figure 4:
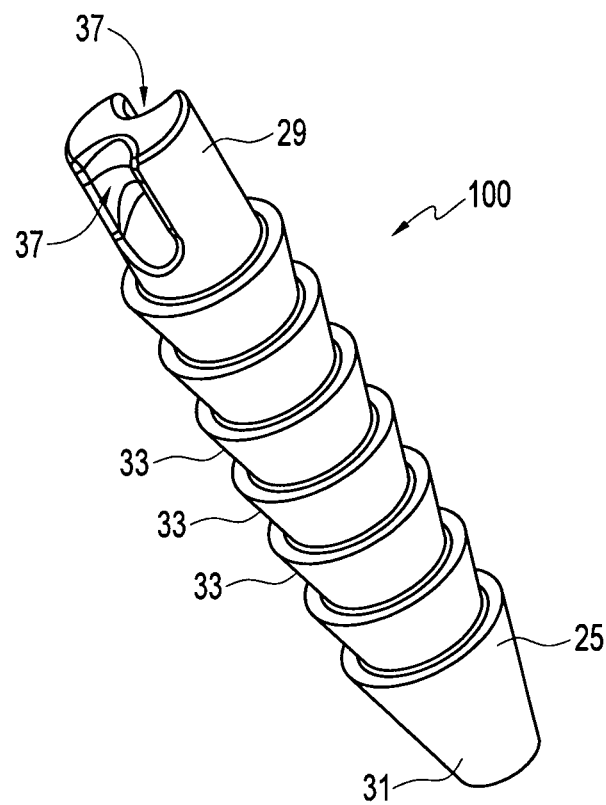
FIG. 4 is an elevational perspective of the suture anchor of FIG. 2.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

Referring now to the drawings, where like elements are designated by like reference numerals, FIGS. 2-8 illustrate a suture anchor 100 of the present invention. The suture anchor 100 includes a molded anchor body 25 having a distal end 12 and a proximal end 13. A length of strand 23 (preferably suture strand) is insert-molded completely within the suture anchor body 25. The anchor body 25 is made up of a moldable material such as a polymer plastic. An exemplary manufacturing process includes insert-molding the strand (preferably suture strand) within the anchor body 25.

Although the embodiments of the present invention will be described and illustrated below with reference to the strand 23 as being a suture strand, and to the anchor body 25 as being a suture anchor body, it must be understood that the invention is not limited to these exemplary embodiments and contemplates embodiments wherein the strand is formed of any flexible material. Accordingly, the invention contemplates embodiments wherein the strand comprises various combinations of suture and/or additional materials, or a plurality of suture strands, for example. In exemplary embodiments, strand 23 may be formed, for example, of a high strength suture material such as the one described in U.S. Pat. No. 6,716,234 to Grafton et al., the disclosure of which is incorporated by reference in its entirety.

The anchor body 25 may be formed of a translucent or transparent polymer material, and is preferably made of bioabsorbable and/or biodegradable materials such as polyglycolic or polylactic acid polymers. Accordingly, suture strand 23 may be visible through the body of the suture anchor 100. Advantageously, the suture strand 23 and the anchor body 25 are made of materials selected such that suture loop or eyelet 27 will not biodegrade before anchor body 25.

In exemplary embodiments, the material making up the molded suture anchor body 25 is polylactic acid (PLA), a commonly used biodegradable polymer material. Other moldable biodegradable materials known in the art, such as PLDLA, can be also used.

As used herein, the term "biodegradable" refers generally to materials that degrade over time in situ. The materials to be included include those described in the relevant literature using terms such as "bioabsorbable" or "bioresorbable," for example. Biodegradable materials may be natural or synthetic. In situ degradation of the material may be full or partial. Degradation can take place by any mechanism and at any rate. Those of ordinary skill in the art would know that biodegradable materials can be blended to take advantage of different inherent properties related to degradation rates and device strength, for example, that the materials exhibit.

Figure 6:
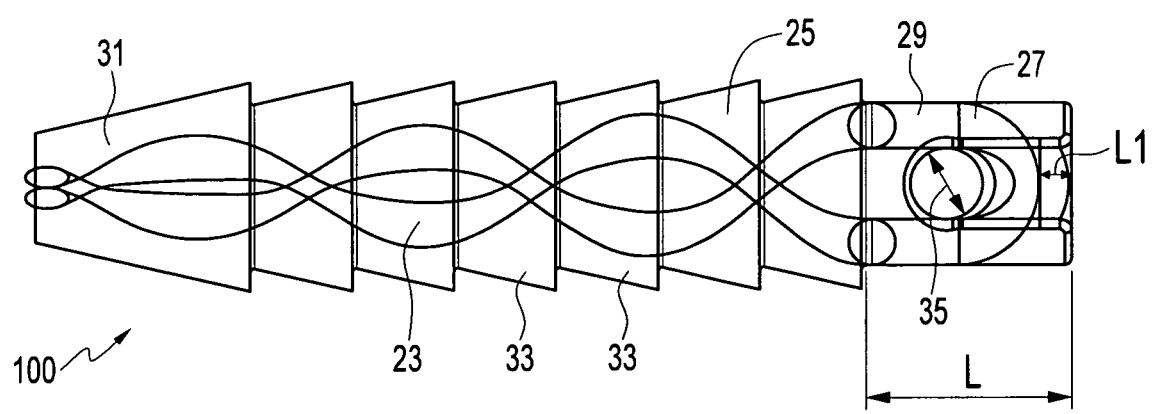
FIG. 6 is a cut-away view of the suture anchor of FIGS. 4 and 5.
Figure 7:
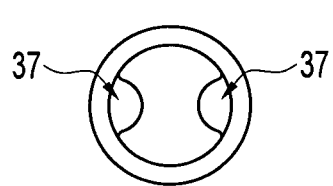
FIG. 7 is a proximal end view of the suture anchor of FIGS. 4-6.
Figure 8:
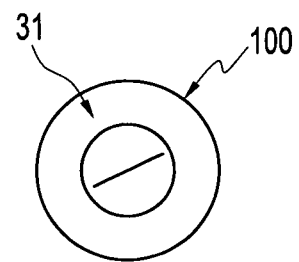
FIG. 8 is a distal end view of the suture anchor of FIGS. 4-7.
Figure 9:
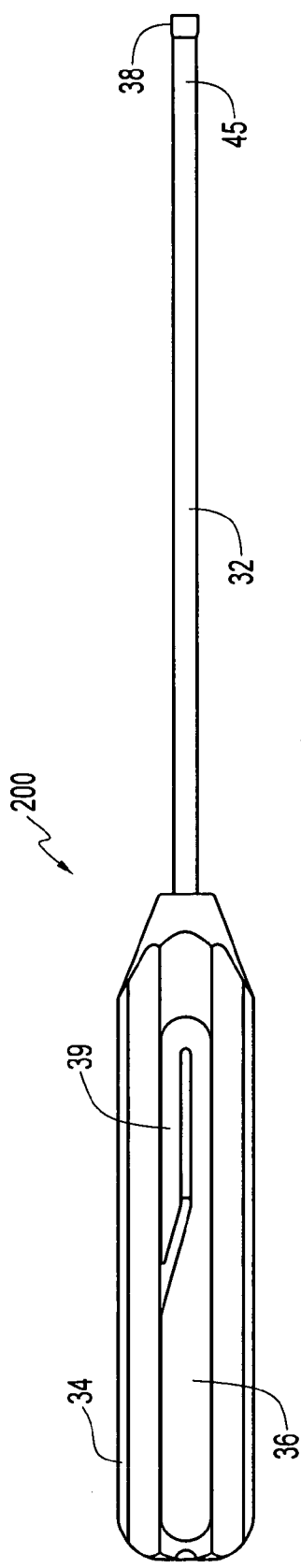
FIG. 9 is a plan view of a hand driver for inserting the suture anchor of the present invention.
Figure 10:
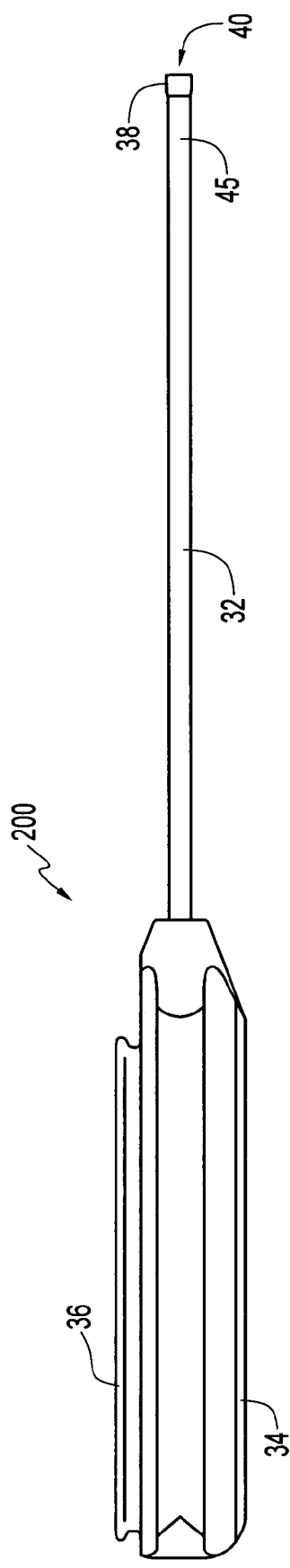
FIG. 10 is an elevation view of the hand driver of FIG. 9.
Figure 11:
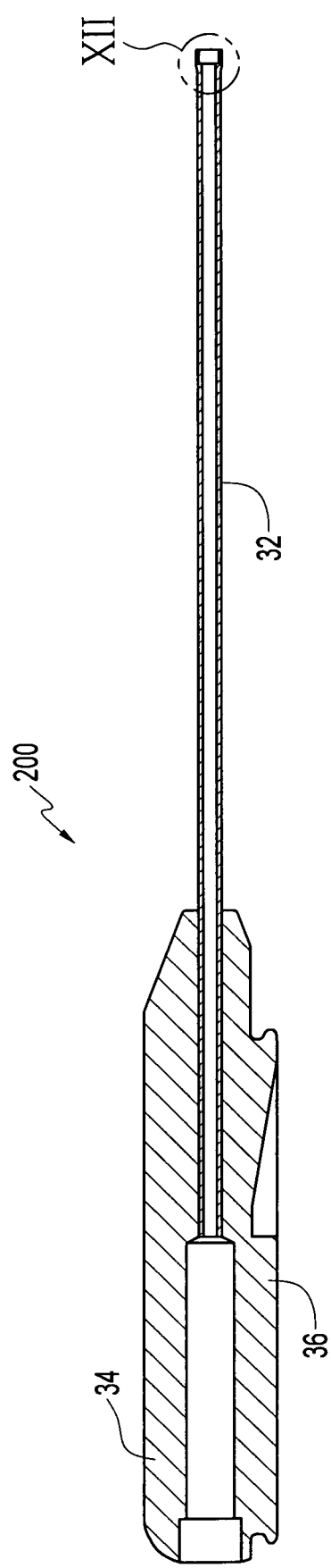
FIG. 11 is a sectional view of the hand driver of FIG. 9.
Figure 12:
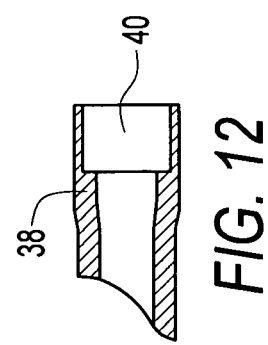
FIG. 12 is a detail view of the drive end of the hand driver of FIG. 9.
Figure 13:
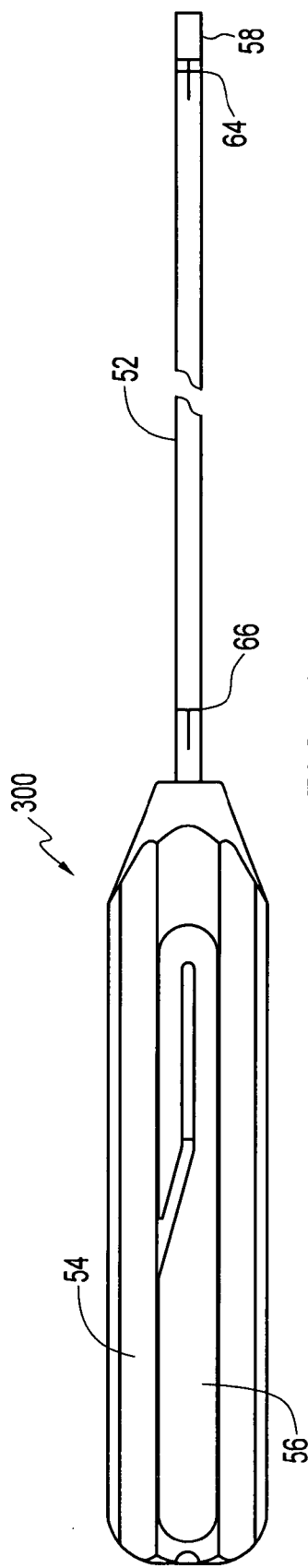
FIG. 13 is a plan view of an alternative hand driver for a method of capsular plication using the suture anchor according to the present invention.
Figure 14:
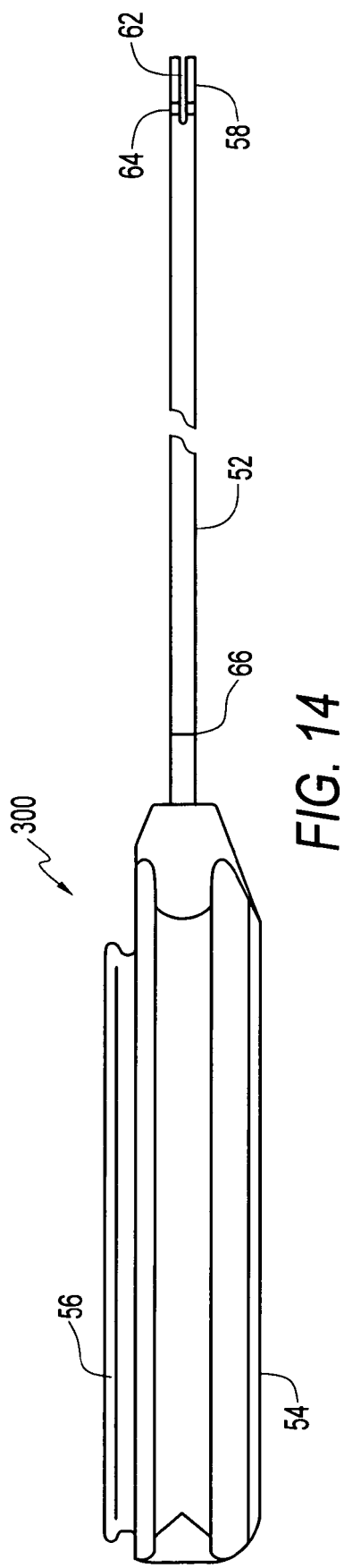
FIG. 14 is an elevation view of the hand driver of FIG. 13.
Figure 15:
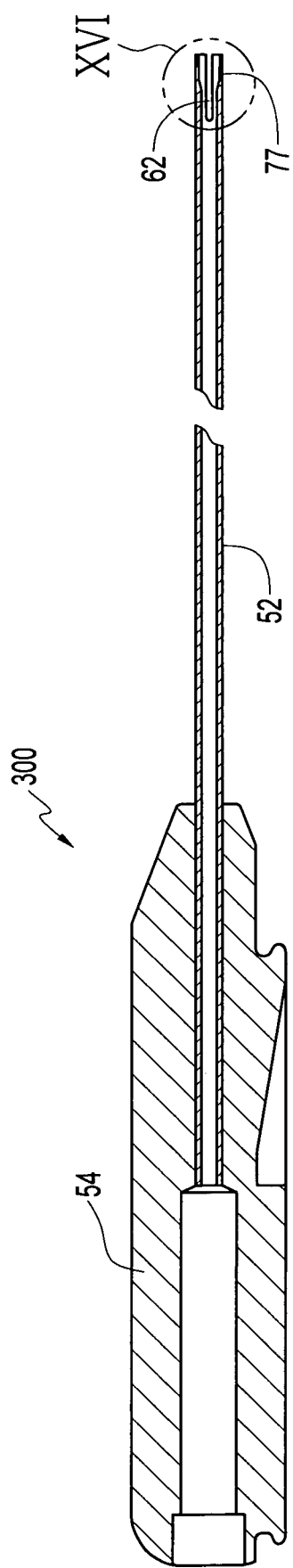
FIG. 15 is a sectional elevation of the hand driver of FIG. 13.
Figure 16:
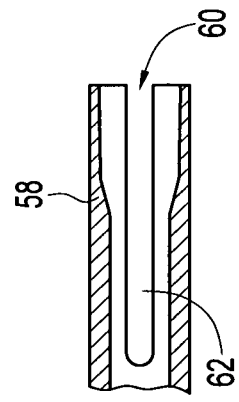
FIG. 16 is a detail view of the drive end of the hand driver of FIG. 13.

As shown in FIG. 6, the length of suture 23 is insert-molded completely within the suture anchor body 25. The length of suture 23 preferably features twists or other surface irregularities to enhance its pullout strength from the suture anchor body 25. Insert-molded suture strand 23 extends through the anchor from the distal end 12 of the suture anchor 100. Suture 23 is molded inside the suture body 25 in the intertwined shape illustrated in FIG. 6, to increase the pullout strength of the suture from the anchor body. The suture forms a loop or suture eyelet 27 located within drive socket 29 at the proximal end 13 of the anchor 100 near eyelet 35. The loop 27 is recessed from the proximal end 13 of the anchor body 25 by a distance $L_1$ (FIG. 6) of about one-third the length L of the drive socket 29 of the anchor, preferably of about one-fourth the length L of the socket 29. The insert-molded suture loop eliminates the need to precisely orientate the eyelet during anchor insertion to optimize suture sliding characteristics.

Strand 23 can be any known type of suture selected according to the size of the anchor and the anticipated application. Strand 23 can be made from biodegradable or non-biodegradable materials. The suture strand 23 is formed to include the looped portion 27 described above. In the preferred embodiment, strand 23 and loop 27 are formed of a high strength suture material such as the one described in U.S. Pat. No. 6,716,234 to Grafton et al., the disclosure of which is incorporated by reference in its entirety. The suture strand 23 may be insert-molded into the anchor in the manner described in U.S. patent application Ser. No. 10/083,568, described above, or U.S. Pat. No. 5,964,783 to Grafton et al., the disclosure of which is incorporated by reference herein.

Figure 5:
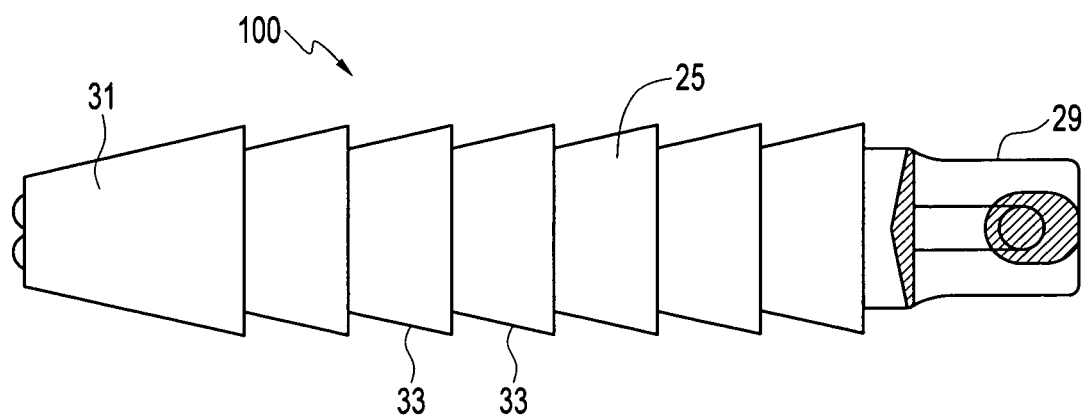
FIG. 5 is a plan view of the suture anchor of FIG. 4.

Suture anchor body 25 features a drive end 29 and an opposing tapered insertion end 31. Preferably, and as illustrated in FIGS. 4-6, the insertion end 31 of the suture anchor 100 tapers to a blunt tip.

Ribs 33 are formed along a central portion of the suture anchor body 25 to enhance fixation within a bone socket, for example. As illustrated in FIGS. 4 and 5, ribs 33 have a truncated, conical shape at an angle of preferably 15° with respect to the longitudinal axis of suture anchor 100. Each rib may increase in diameter progressively toward the head of suture anchor 100, reaching a major diameter of about 3.0 mm, for example. Barbs, slots, screw threads, or other anchoring structures, could be formed instead of, or in addition to, ribs 33. These structures, if provided in addition to the ribs, afford access for ingrowth of bony tissue for enhanced pullout strength.

The looped portion 27 of the suture 23 is insert-molded within the drive end 29. The looped portion 27 is formed around an eyelet 35 developed as an opening through the drive end 29. Two suture relief grooves 37 (FIGS. 4 and 7) intersect the eyelet and allow additional strands (e.g., suture strands) threaded through the eyelet 35 (for tissue attachment) to extend proximally back from the suture anchor 100 without impeding engagement between the drive head 29 and a hand driver used to install the suture anchor 100. The additional suture strand, or plurality of suture strands, may be FiberWire composite sutures of alternating colors to maximize repair strength, aid in suture management and provide superior tying characteristics. Optionally, suture anchor 100 of the present invention can be distributed with at least one strand of suture already threaded through the eyelet 35 and grooves 37.

The drive end 29 of the suture anchor body 25 can be tapered for a snug fit into the hand driver. The drive head also can be shaped for rotational engagement with the hand driver.

FIGS. 9-16 illustrate various embodiments of drivers 200, 300 used to install the suture anchor 100 of the present invention. FIGS. 9-12 illustrates cannulated driver 200 which may be preloaded with the suture anchor 100 of FIGS. 2-8 and with suture strands attached to the eyelet 35. As explained in more detail below with reference to FIGS. 9-12, the suture strands are threaded through the cannula of the driver 200 and secured on a hook on the handle of the driver, to allow the proximal end of anchor 100 to be received by a recess in the cannula of the driver 200 so that the suture anchor is driven into a pilot hole.

Hand driver 200 (FIGS. 9-12) according to a first embodiment of the present invention includes a cannulated shaft 32 provided with a cannulated handle assembly 34 and a drive head 45. As detailed below, cleat 36 is provided on the handle assembly 34 for securing suture attached to the eyelet on the suture anchor 100 and passed through the cannulated shaft and handle. The distal tip 38 of the drive head 45 provides a recess 40 which is configured to receive the proximal end 13 of the suture anchor 100 of FIGS. 2-8. The outer diameter of the distal end of the driver 200 is preferably less than or equal to the maximum outer diameter of the suture anchor 100. In an exemplary embodiment, the drive head 35 is rectangularly shaped and has a width and a length which substantially corresponds to the width and length of drive end 29 of suture anchor 100. Preferably, the drive head is slightly shorter and has a slightly larger width than drive end 29, so that the fit is not too tight, yet ensures secure engagement for driving the suture anchor 100 into bone.

The shaft 32 preferably comprises an elongate, narrow diameter body suitable for use in remote procedures performed through percutaneous tissue punctures, such as arthroscopic, laparoscopic and other invasive procedures and the like. The shaft typically has a length of about 5 cm to about 20 cm, preferably about 15 cm. The diameter of the shaft assembly is sufficiently small to facilitate introduction through access sheaths, cannulas, trocars, and the like, typically being less than about 10 mm, preferably about 5 mm.

The handle assembly 34 preferably includes an elongated double hook 39 extending substantially along the length thereof and having a hook at the proximal end and at the distal end thereof, and a clip 36 formed at one end region of the double hook 39. When driver 200 is engaged with suture anchor 100, excess lengths of suture passed through the proximal end of driver 200 can be wrapped around the double hook 39, and the ends of the sutures can be secured in the clip 36. In this manner, the suture strands can be prevented from becoming tangled or otherwise interfering with the surgeon's work.

Driver 200 is preferably constructed to withstand an application of about 20 in/lb of torque. Preferably, although not necessarily, at least the shaft and drive head are made of stainless steel. However, other materials may be used which provide the necessary strength and rigidity for installing the suture anchor of the present invention into cortical bone.

The anchor 100 and driver 200 may be provided to the surgeon as a preformed assembly with the suture strands pre-threaded through eyelet 35 and through the cannula of the driver and secured on the handle. During surgery, for example, the suture anchor 100 is urged into a hole formed in bone. The hole can be formed using a punching or boring tool, for example, driven into the bone. Advantageously, the hole formed in the bone is made deep enough, and the suture anchor 100 is advanced into the hole sufficiently, so that the proximal end of the anchor sits flush with or below the bone surface. Accordingly, the repair leaves a smooth bone surface, minimizing or eliminating abrasion or other damage to surrounding soft tissue.

The anchor generally becomes encapsulated by fibrous tissue within six weeks after implantation. Although PLDLA is the most preferred material for the suture anchor of the present invention, as detailed above, other bioabsorbable materials known in the art can be utilized. Preferably, the anchor material is selected so as to absorb or degrade substantially completely within 12-16 months of implantation.

Suture anchors according to the present invention can be used for arthroscopic procedures. The anchors also are advantageous for open and mini-open surgical procedures. Specific examples of applicable procedures include cortical bone-soft tissue fixation, Bankart and SLAP shoulder repairs.

The suture anchor 100 of the present invention is particularly well suited for reattachment of the glenoid labrum or inferior glenohumeral ligament in patients with primary or recurrent anterior dislocation or subluxation of the shoulder in association with adequate post-operative immobilization. More specifically, the anchor also can be used for repair procedures such as capsulolabral plication, as described below, and in conjunction with a second exemplary embodiment of a driver 300 used in the method of installing anchor 100 of the present invention.

FIGS. 13-16 illustrate details of the second exemplary embodiment of driver 300 used to install the suture anchor 100 of the present invention during an arthroscopic procedure, preferably during an open procedure such as mini-open rotator cuff repairs. The driver 300 is different from the driver 200 described above in that driver 300 comprises a slot or side cannulation at the distal tip of the cannulated shaft and defined by break edges 77. Preferably, driver 300 is employed in capsule plication applications using the anchor 100 of the present invention. Capsulolabral plication is indicated for repair of certain types of shoulder laxity. When pathologically increased anterior laxity is combined with a Bankart lesion, for example, the addition of a capsular plication to the reattachment of the capsulolabral avulsion is recommended.

Driver 300 of FIGS. 13-16 includes a cannulated shaft 52 provided with a cannulated handle 54. As in the previously-described embodiment for driver 200, cleat 56 of driver 300 is provided on the handle for securing suture attached to the eyelet of the anchor and passed through the cannulated shaft and handle. The distal tip 58 of cannulated shaft 52 provides a recess 60 which receives the proximal end of suture anchor 100. Recess 60 is defined by break edges 77. The outer diameter of the distal end of the driver 300 is preferably less than or equal to the maximum outer diameter of the suture anchor. As illustrated in FIGS. 13-16, driver 300 also features a slot 62 which is continuous with recess 60.

An exemplary method of capsular plication proceeds using a 36-inch (91.4 cm) long #2 suture to plicate the capsulolabral complex. Both free ends of the suture are brought out an operative cannula. A spear with an included obturator is introduced through a skin incision or a clear cannula. The tip of the spear is positioned on bone and the obturator is removed. A pilot hole is prepared in bone using either a punch or a drill depending on the surgeon's preference. With the manual punch, a mallet is used to advance the punch into bone until the punch handle meets the back of the spear and/or the shoulder on the distal part of the punch meets the bone surface. Alternatively, the drill can be attached with a Jacob chuck to a motorized drill and advanced until the stop on the drill bit meets the back of the spear.

After the pilot hole is created and the punch or drill is removed, the sterile-packaged anchor 100 is opened to the sterile field using appropriate sterile technique. The anchor is removed and the suture is unloaded from the implant. A separate sterile packaged plication driver 300 is opened to the sterile field. One of the two legs of the plication suture is selected. This suture leg is the one on the medial side, or the one that passes under the tissue.

The selected suture leg is loaded through the anchor eyelet. The anchor 100 is positioned on plication driver 300 so that the open side of the eyelet 35 faces the open slot 62 on the driver. The suture leg will exit the slot 62 on the driver 300. The anchor 100 with driver is introduced into the prepared pilot hole by hand. A mallet may be used to advance the implant into the hole. The anchor is advanced until a second laser line 64 on the distal tip of the driver is flush with the bone surface and a laser line 66 on the proximal part of the anchor driver shaft is flush with the back of the spear handle.

The handle is pulled straight off the anchor 100 and the spear is removed. Additional anchors are inserted depending upon the size of the soft tissue defect. Suture passing and knot tying are carried out in the preferred fashion.

Advantageously, when the suture anchor 100 is inserted into bone, it is not necessary for the proximal end of the anchor to be countersunk below the bone surface, as is required with prior art devices to prevent tissue abrasion by the exposed eyelet. Consequently, the anchor of the present invention does not need to be inserted as far as the prior art devices. Further, the internally disposed suture eyelet avoids abrasion of the rim of bone. In addition, because the suture anchor of the present invention is provided with a plurality of ribs extending the full body anchor, better fixation in bone is achieved. Finally, the intertwined suture in the present invention provides greater pull-out strength than prior suture anchors.

Although the present invention has been described in relation to particular embodiments thereof, many other variations and modifications and other uses will become apparent to those skilled in the art. The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. An insert-molded suture anchor, comprising:
   a ribbed body formed of a biodegradable polymer, the ribbed body having a longitudinal axis, a proximal end and a distal end, the ribbed anchor body being provided with a plurality of adjacent, truncated cones and terminating at its distal end in a truncated cone with a blunt tip;
   an eyelet formed in a drive end provided at the proximal end of the anchor, the eyelet being formed as an opening through the drive end, the drive end being configured to be received in a driver head of a driver, so that the drive end of the anchor is received in a recess in a cannula of the driver head; and
   a suture completely insert molded within the anchor, the suture including an insert-molded portion in the form of a loop disposed around the eyelet at the drive end of the suture anchor body, the loop being totally contained within the polymer of the body.

2. The insert-molded suture anchor of claim 1 further comprising two diametrically opposite apertures provided within the drive end of the anchor, the apertures intersecting at least a portion of the eyelet.

3. The insert-molded suture anchor of claim 2, wherein the apertures are oriented about parallel to the longitudinal axis of the ribbed body.

4. The insert-molded suture anchor of claim 1, wherein the eyelet has a circular cross-sectional configuration.

5. The insert-molded suture anchor of claim 1, wherein the suture loop is recessed from the proximal end of the anchor by about one fourth the length of the drive end.

6. The insert-molded suture anchor of claim 1, further comprising at least one strand attached to the eyelet.

7. The insert-molded suture anchor of claim 1, wherein the ribbed body comprises bioabsorbable material.

8. A suture anchor formed by a process comprising the steps of:
   placing at least one strand of suture in a mold;
   molding a suture anchor body completely surrounding the suture by delivering an uncured polymer into the mold, wherein the molded suture anchor has an eyelet formed in a drive end, the eyelet being formed as an opening through the drive end, and the suture forms a loop inside the polymer of the drive end of the suture anchor body and around the eyelet; and
   causing the polymer to cure to allow the loop of the suture to be totally contained within the polymer.

9. The suture anchor of claim 8, wherein the suture loop is recessed from a proximal end of the anchor by about one fourth the length of the drive end.

10. The suture anchor of claim 8, wherein the strand of suture is provided with irregularities.

\* \* \* \* \*